United States Patent
Aldefeld et al.

(10) Patent No.: US 6,813,512 B2
(45) Date of Patent: Nov. 2, 2004

(54) METHOD AND APPARATUS FOR INTRAVASCULAR LOCALIZATION AND IMAGING WITHOUT X-RAYS

(75) Inventors: Bernd Aldefeld, Hamburg (DE); Friedrich-Karl Beckmann, Pinneberg (DE); Holger Eggers, Kaltenkirchen (DE); Rolf Udo Dieter Kobs, Hamburg (DE); Erhard Paul Artur Klotz, Neumuenster (DE); Michael Harald Kuhn, Hamburg (DE); Dirk Manke, Hamburg (DE); Volker Rasche, Hamburg (DE); Georg Weidinger, Hamburg (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/976,328

(22) Filed: Oct. 12, 2001

(65) Prior Publication Data

US 2002/0077546 A1 Jun. 20, 2002

(30) Foreign Application Priority Data

Oct. 17, 2000 (DE) ........................................ 100 51 244

(51) Int. Cl.$^7$ ................................................. A61B 5/00
(52) U.S. Cl. ...................... 600/410; 600/411; 600/424; 600/426; 600/427; 600/437; 600/438; 600/476
(58) Field of Search ............................... 600/407, 410, 600/411, 422–427, 437, 438, 476

(56) References Cited

U.S. PATENT DOCUMENTS

| 5,638,819 A | | 6/1997 | Manwaring et al. | |
|---|---|---|---|---|
| 5,951,472 A | * | 9/1999 | Van Vaals et al. | 600/411 |
| 6,023,636 A | * | 2/2000 | Wendt et al. | 600/410 |
| 6,266,552 B1 | * | 7/2001 | Slettenmark | 600/424 |
| 6,275,724 B1 | * | 8/2001 | Dickinson et al. | 600/424 |
| 6,498,948 B1 | * | 12/2002 | Ozawa et al. | 600/476 |
| 2002/0165448 A1 | * | 11/2002 | Ben-Haim et al. | 600/424 |

* cited by examiner

Primary Examiner—Ruth S. Smith
(74) Attorney, Agent, or Firm—John C. Vodopia

(57) ABSTRACT

A device for determining the position of a medical instrument that is introduced into an object to be examined is also used for imaging the vicinity of the medical instrument. In order to enable the acquisition of instantaneous position information and image information from the vicinity of the medical instrument for all kinds of medical instruments, a localization device that is arranged in the end zone of the medical instrument that is to be introduced determines the position of the medical instrument within the object to be examined; at the same time image information is acquired in the vicinity of the medical instrument by an image acquisition device that is arranged on the medical instrument and on the basis of the position thus determined the position of the medical instrument (3) is reproduced in a survey image of the object to be examined and images of the vicinity of the object to be examined are displayed on the basis of the image information acquired.

14 Claims, 1 Drawing Sheet

METHOD AND APPARATUS FOR INTRAVASCULAR LOCALIZATION AND IMAGING WITHOUT X-RAYS

BACKGROUND OF THE INVENTION

The invention relates to a method for determining the position of a medical instrument introduced into an object to be examined and for imaging the vicinity of the medical instrument. The invention also relates to a corresponding device as well as to a corresponding medical instrument and to a computer program.

U.S. Pat. No. 5,638,819 discloses a method via which a medical instrument, notably a biopsy needle or an endoscope, can be introduced into a patient along a desired trajectory, notably into the brain of a patient. For the localization of the instrument a sensor is arranged at the end of the instrument which is not introduced into the patient; the position of this sensor relative to a reference co-ordinate system can be determined by means of an appropriate measuring device. For the navigation of the instrument the position thereof is reproduced in a two-dimensional tomographic image while a live video image of the endoscope is displayed at the same time. However, the known method is suitable only for the localization and navigation of rigid medical instruments, because it is only in the case of a rigid instrument that reliable information concerning the position of the part of the instrument that is present within the patient can be derived from the position of the sensor arranged on the part of the instrument that is situated outside the patient.

OBJECTS AND SUMMARY OF THE INVENTION

Therefore, it is an object of the present invention to provide a method and a device which enable localization and navigation of any medical instrument introduced into an object to be examined.

In accordance with the invention this object is achieved by means of a method wherein the position of the medical instrument within the object to be examined is determined by means of a localization device that is arranged in the end zone of the medical instrument that is to be introduced, image information concerning the vicinity of the medical instrument being acquired at the same time by means of an image acquisition device arranged on the medical instrument, the position of the medical instrument being reproduced in a survey image of the object to be examined on the basis of the position determined, and images of the vicinity of the object to be examined which are associated each time with the relevant position being displayed on the basis of the image information acquired.

This object is also achieved by means of a device which includes localization means for determining the position of the medical instrument in the object to be examined, a localization device being arranged in the end zone of the medical instrument that is to be introduced, imaging means for the acquisition at the same time of image information concerning the vicinity of the medical instrument, an image acquisition device being arranged on the medical instrument, and data processing and display means for determining and displaying the position of the medical instrument in a survey image of the object to be examined, that is, on the basis of the position thus determined, and for determining and displaying images of the vicinity of the object to be examined, said images being associated with the relevant position, on the basis of the image information acquired.

The invention is based on the idea that, as opposed to the known method, notably in the case of flexible medical instruments, for example catheters which are used above all for intravascular interventions, it is not possible to arrange a localization device for determining the medical instrument on the part of the instrument that is not introduced into the object to be examined. This is because in that case the mounting of optical sensors or markers on the end of a catheter which projects from the object to be examined and the determination of the position of these sensors or markers, for example by means of an optical position measuring system, would not provide reliable information as regards the position of the tip of the catheter or the course of the catheter introduced into the object to be examined. Therefore, in accordance with the invention the localization device is arranged in the zone of the medical instrument which is also introduced into the object to be examined, notably in the inserted end zone of the medical instrument, because particularly the position thereof during the intervention is of interest. In order to acquire also image information from this zone at the same time, in accordance with the invention it is also proposed to arrange in said zone an image acquisition device which serves to acquire image information concerning the vicinity of the introduced medical instrument simultaneously with the determination of the position thereof. The image information and the position information thus acquired is used in accordance with the invention to display the instantaneous position of the medical instrument each time in a survey image of the examination zone, for example in an angiogram or in a so-called Road Map in the case of an intravascular intervention, and to display at the same time one or more instantaneous images of the vicinity of the medical instrument.

In accordance with an advantageous version the survey image may be formed from a three-dimensional or four-dimensional image data set, the four-dimensional image data set having a temporal resolution in addition to the spatial resolution. This means that different image data sets are obtained at different instants, for example, during the cardiac motion phase; in such different image data sets above all different positions of the anatomy examined at the various instants are taken into account or corrected. The image data sets themselves may have been acquired by means of an arbitrary imaging method, for example, by means of magnetic resonance tomography, computed tomography, an X-ray method, notably a three-dimensional rotation X-ray method, or by means of an ultrasound method.

Furthermore, the survey image may be advantageously formed from a motion-compensated image data set for which notably the cardiac motion and/or the respiratory motion is compensated; such motions have different effects on the anatomy in dependence on the region examined. Appropriate methods are known for such compensation. For example, for the compensation of the cardiac motion it is possible to form an electrocardiogram during the acquisition of the image data in order to associate the image data with a respective given cardiac phase and to correct the effects of the cardiac motion on the anatomy in the individual cardiac motion phases on the basis of a cardiac model. For the correction of the respiratory motion there are appropriate models and sensors that monitor the respiratory motion and determine and compensate the effects thereof on the anatomy.

Various advantageous embodiments of the localization device used. This device may be a magnetic field sensor whose position is determined by means of an external measuring device, or an active or a passive microcoil whose position can be determined by means of a magnetic resonance device, or also an ultrasound sensor which can be detected by means of an ultrasound device. Moreover, the medical instrument may also consist at least partly of a material that can be detected by means of an ultrasound device or a magnetic resonance device. Also feasible is any other punctiform signal source that can be arranged on the medical instrument and whose signal can be detected by an external detector device so as to determine the position of the signal source therefrom.

Advantageous further possibilities for the use of an image acquisition device are provided. That is, it is a common aspect of all image acquisition devices that they are preferably arranged in the end zone of the medical instrument that is to be introduced, because notably image information from this region is of interest. The transfer of the acquired image data may take place in a contactless manner or via leads. Many further embodiments of the image acquisition device additionally require external image acquisition means for the acquisition of image information. For example, one embodiment of the MR device which is preferably implemented as a microcoil requires an external excitation coil as it is used in a magnetic resonance tomography device. Other further embodiments, for example an internal excitation and measuring coil, an endoscope or an intravascular ultrasound device, however, do not require additional external image acquisition means.

For the navigation and continuous monitoring of the position of the medical instrument during an intervention, the localization and imaging are preferably performed continuously or at regular intervals, the instantaneous position and the associated images being displayed each time.

It is particularly advantageous to use the invention for the navigation in blood vessels such as, for example the coronary vessels, during an intravascular intervention. The invention, however, can also be used for navigation in other cavities of an object to be examined, for example in the intestine or the esophagus of a patient.

The invention is used particularly advantageously in conjunction with flexible medical instruments such as, for example catheters as used notably also for the examination and treatment of coronary vessels. The invention provides the physician with instantaneous information concerning the position of the catheter as well as with image information from the end zone of the catheter during the travel of the catheter inside the patient, thus enabling very precise navigation in reaching the target area.

The invention also relates to a corresponding device for determining the position of a medical instrument in an object. The invention furthermore relates to a medical instrument to be introduced into an object to be examined, which instrument includes a localization device that is arranged in the end zone that is to be introduced and serves to determine the position of the medical instrument in the object to be examined, and also includes an image acquisition device for the simultaneous acquisition of image information concerning the vicinity of the medical instrument, the position determined being intended for use in determining and reproducing the position of the medical instrument in a survey image of the object to be examined and the acquired image information is intended to form and reproduce images of the vicinity of the object to be examined which is associated with the relevant instantaneous position. The device as well as the medical instrument may be elaborated in accordance with the invention so as to form advantageous embodiments which are identical or analogous to the versions disclosed above for the method.

The invention also relates to a computer program with program sections for executing the method in accordance with the invention and/or for controlling the device in accordance with the invention or the medical instrument in accordance with the invention during execution of the computer program by a computer.

BRIEF DESCRIPTION OF THE DRAWING

The invention will be described in detail hereinafter with reference to the sole FIGURE which is a schematic diagram of a system according to the invention.

DETAILED DESCRIPTION OF THE PREFERRED EMBODIMENT

Figure 1:
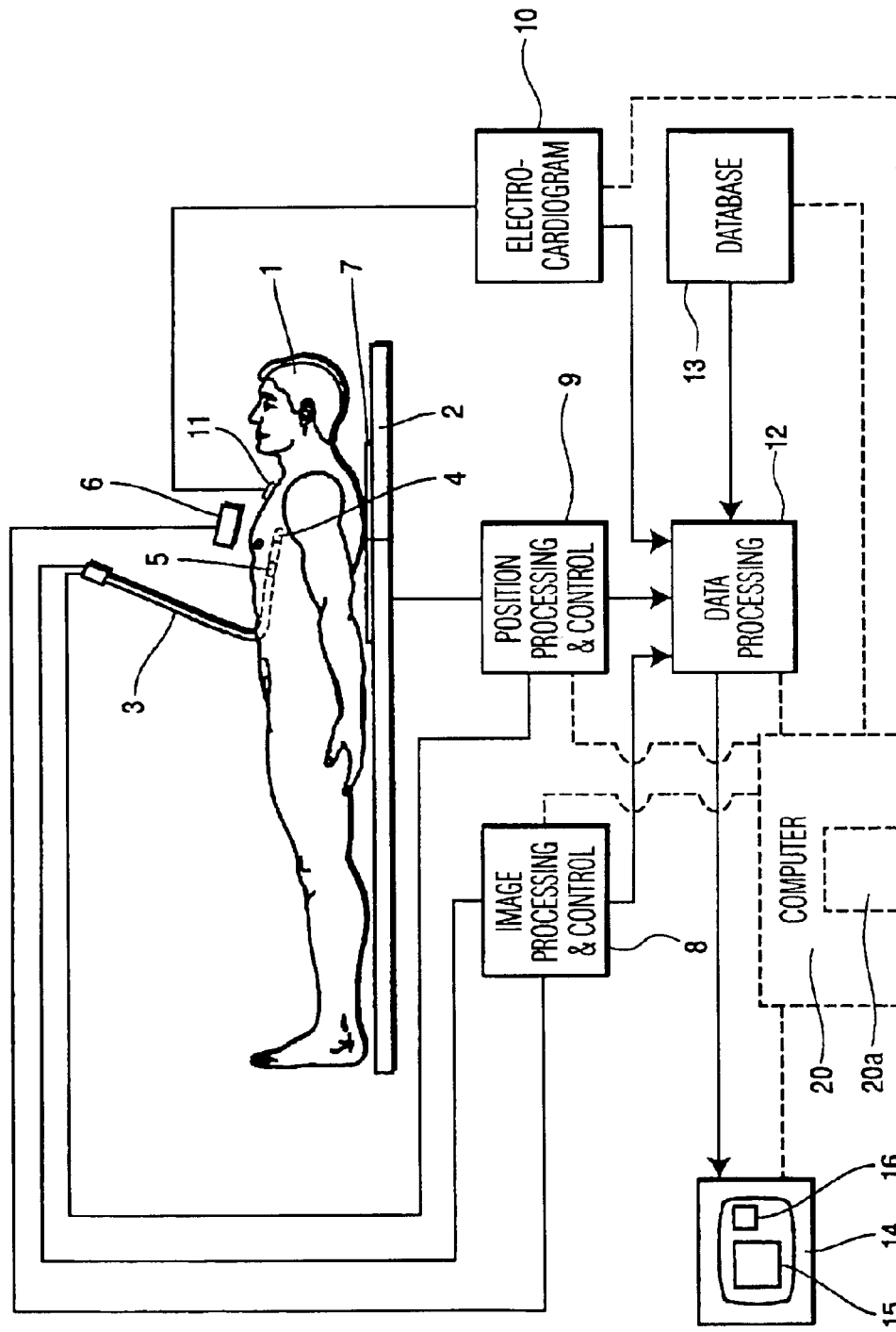

The block diagram in the figure shows the essential elements of a device in accordance with the invention. A recumbent patient 1 is arranged on a patient table 2 in order to perform an intravascular intervention in this device. A catheter 3 in accordance with the invention is introduced into a main artery of the patient 1 for a treatment of the coronary arteries and is advanced as far as the coronary vessels by a physician. The end zone of the catheter which is introduced into the patient 1 is provided with an image acquisition device 4 and a localization device 5. It is assumed that the image acquisition device 4 of the embodiment shown is formed by a microcoil which, after excitation by an external excitation coil 6, can receive magnetic resonance (MR) signals from its vicinity, said signals supplying image information concerning the vicinity of the image acquisition device 4. This procedure is known per se, like a magnetic field coil for generating a steady magnetic field (not shown), from the field of magnetic resonance tomography, so that it will not be elaborated herein.

Furthermore, in the end zone of the catheter 3 there is arranged a localization device 5 which is assumed to be constructed as a magnetic field sensor in the embodiment shown; such a sensor co-operates with a coil array 7 that is arranged underneath the patient 1. Using the signals emitted by the individual coils of the coil array 7, the position of the magnetic field sensor, and hence the position of the end zone of the catheter 3, can be determined on the basis of the signals received from the magnetic field sensor 5. This method of determining a position is also known per se and will not be elaborated herein.

An image processing and control device 8 is provided for the processing of the signals received by the microcoil 4 and for the control of the microcoil 4 and the excitation coil 6; this device converts the measured signals into image information and applies this information to a data processing device 12. A position processing and control unit 9 is provided so as to process the signals acquired by the magnetic field sensor 5 and to control the magnetic field sensor and the coil array 7; this unit converts the measured signals into position data which is applied to the data processing device 12.

Moreover, in order to correct the measured position data and image data in respect of cardiac motion there is provided an electrocardiogram device 10 which includes one or more appropriate sensors 11 and produces an electrocardiogram in parallel with the determination of the position and the image data acquisition. This data is also applied to the data processing device 12.

The data processing device 12 determines, on the basis of the data received, the position of the magnetic field sensor 5, and hence the end zone of the catheter 3, in relation to a stored image data set of the examination zone of the patient 1. This image data, formed directly before the intervention or during an earlier diagnosis, is stored in a database 13 which is accessible by the data processing device 12. In order to enable determination of a current position of the magnetic sensor 5 relative to a survey image derived from the database 13, moreover, suitable registration is required, for example by means of suitable markers on the patient which are also present in the survey images and are marked as reference points directly before the intervention. In the embodiment shown, relating to an intravascular intervention, a three-dimensional angiogram (a so-called road map) of the coronary vessels is preferably used as the survey image. Finally, the data processing device 12 applies the image information to a display device, for example a monitor 14 on which the survey image 15 in which the current position of the magnetic field sensor 5 or the tip of the catheter 3 is also superposed is displayed on one side. Moreover, the instantaneous image 16 of the vicinity of the catheter tip, formed from the data acquired by the microcoil 4, is displayed adjacently so as to supply the physician with additional information enabling him to determine where the catheter tip is situated at the relevant instant, thus enabling better navigation. No X-ray device is then required for the acquisition of image information, that is, notably no fluoroscopy device which would permanently expose the patient to X-rays during the acquisition of information.

A computer 20 having a computer program 20a on a computer readable medium may be connected to the data processing device 12, the position processing and control device 9, the image processing and control device 8, the database 13, and the monitor 14 for controlling the device and or the medical instrument of the present invention.

The embodiment of the device in accordance with the invention that is shown in the Figure constitutes merely one version of such a device and has been described on the basis of actual examples of the means used. Numerous other versions are feasible in respect of the type, construction and arrangement of the means used, some of which will be described in detail hereinafter.

Additionally, sensors for measuring the respiratory and/or cardiac motion may be fitted on the patient 1 so as to enable compensation of motions of the anatomy during the localization and imaging.

The survey image may be formed from a spatially resolved three-dimensional image data set or from a spatially and temporally resolved four-dimensional image data set having an adequate spatial resolution, the image data set already being available during the intervention. There are various modalities for forming such an image data set. Notably MRI (Magnetic Resonance Imaging), CT (Computed Tomography), 3D-RX (3D Rotational X-ray) and ultrasound techniques are the most promising techniques for the acquisition of image data of the coronary arteries and for the formation of high-resolution angiograms.

Moreover, it must be possible to image the local anatomy and notably the vessel wall at the tip of the catheter practically in real time during an intervention, or to deliver image data thereof. The possibility of looking ahead inside the artery, that is, in the direction of travel of the catheter, is also very important in the event of problems such as, for example jamming of the catheter or for choosing the correct course at bifurcations of the arteries. In order to satisfy these requirements, the following possibilities can be considered:

a) Intravascular Ultrasound (IVUS) at the moment offers two-dimensional ultrasound sensors which are capable of supplying image information in the radial direction around the longitudinal axis of the catheter. However, three-dimensional ultrasound sensors that are capable of supplying image information from all three spatial directions are also feasible.

b) Optical Coherence Tomography (OCT) enables image data to be acquired with a very high spatial resolution. This technique, utilizing simple optics at the tip of the catheter, also enables the realization of non-orthogonal viewing angles.

c) In the case of Intravascular Magnetic Resonance Imaging (IVMRI) one or more receiving coils in the form of microcoils are arranged on the catheter, the RF excitation being realized (as shown in the Figure) by means of an external excitation coil or by means of an internal excitation coil. However, in that case a strong magnet is also required in order to generate a strong main magnetic field; such a magnet limits the access to the patient and makes the device very expensive.

d) Endoscopes can also be used as image acquisition means; granted, such endoscopes do not supply image data concerning the wall of the vessel, but they do enable looking in the forward direction.

There are also various possibilities in respect of the localization device; some preferred versions thereof are given hereinafter:

a) Magnetic field sensors are very promising, because they are already being used in miniaturized form and enable very exact determination of the position.

b) Active or passive microcoils that operate on the basis of MR can also be used for determining the position.

c) An ultrasound sensor may also be arranged on the catheter as a localization device, the ultrasound sensor then being integrated in the probe of an ultrasound scanner by way of a Catheter System Interface (CSI). When the ultrasound sensor in the catheter is reproduced by the ultrasound scanner, the interface (CSI) injects a bright arrow in conformity with its position. Because this represents only the position of the catheter relative to the ultrasound device, it is additionally necessary to determine the position of the ultrasound device in order to convert the positions determined into positions relative to a co-ordinate system of the image data present. The medical instrument may also be provided with a punctiform ultrasound source whose signals are detected by an external sensor.

d) Catheters that are enrobed in a special manner and can be made visible by way of ultrasound can also be used. This also makes it possible for the entire catheter instead of only its tip to be localized and reproduced in a survey image. A passive susceptibility catheter may also be used.

For the visualization during the intervention the complete information must be reproduced in a suitable manner. Instead of a standard television apparatus or monitor use can be made of, for example head-mounted displays, for example in the form of special looking glasses that give the physician the impression as if he or she is looking into the patient. Different display modes and viewing angles should also be possible. Preferably, the image data acquired from the interior of the anatomy is displayed on-line and quasi as video. However, it is also possible to generate and display only still images at regular intervals and/or a plurality of images from different viewing angles.

Moreover, suitable interfaces for simple operation should also be available in order to enable simple switching over between different modalities and image display modes. Control by way of speech or gestures is also feasible. Additionally, for cases of emergency a simple X-ray system or other imaging device may be kept on standby duty.

The invention thus enables continuous determination of the instantaneous position of the medical instrument during an intervention and acquisition of image information from the vicinity of the medical instrument. Moreover, the position is superposed on a survey image acquired in advance so as to facilitate navigation of the medical instrument. The exact construction of the means used is dependent notably on the type of intervention desired and on the type of examination zone. The invention is suitable not only for flexible medical instruments such as, for example catheters, but in principle also for any instrument that can be introduced into a patient and whose position is to be accurately determined from the outside.

What is claimed is:

1. A method for determining the position of a medical instrument introduced into an object to be examined and for imaging the vicinity of the medical instrument, comprising the steps of displaying a survey image of the object to be examined, the survey image of the object being stored in a memory and including indications of markers on the patient;

determining the position of the medical instrument within the object to be examined by a localization device that is arranged at an end zone of the medical instrument, the end zone comprising a portion of the medical instrument that is to be introduced into the object during use of the medical instrument, acquiring image information of the vicinity of the medical instrument, at the same time as said step of determining, using an image acquisition device arranged on the medical instrument, reproducing the position of the medical instrument in the survey image of the object to be examined on the basis of the position determined and the markers on the patient indicated in the survey image, and displaying images of the vicinity of the object to be examined which are associated each time with the relevant position on the basis of the image information acquired.

2. The method as claimed in claim 1, wherein the localization device comprises at least one magnetic field sensor whose position is determined by an external measuring device.

3. The method as claimed in claim 1, wherein the localization device comprises at least one active or passive microcoil whose position is determined by a magnetic resonance device.

4. The method as claimed in claim 1, wherein the localization device comprises an ultrasound sensor.

5. The method as claimed in claim 1, wherein the medical instrument consists at least partly of a material that can be detected by one of an ultrasound device or a magnetic resonance device.

6. The method as claimed in claim 1, wherein the image acquisition device is an ultrasound device.

7. The method as claimed in claim 1, wherein the image acquisition device comprises an optical coherence tomography device.

8. The method as claimed in claim 1, wherein the image acquisition device comprises an MR device.

9. The method as claimed in claim 1, wherein the image acquisition device comprises an endoscope.

10. The method as claimed in claim 1, further comprising the step of correcting the measured position data in response to cardiac motion detected by a electrocardiogram device.

11. The method as claimed in claim 1, further comprising the step of acquiring the survey image by one of magnetic resonance imaging, computed tomography, 3-D rotational X-ray and ultrasound techniques.

12. The method as claimed in claim 11, wherein said step of acquiring the survey image includes acquiring a four-dimensional image data set having a temporal resolution including image data sets at different instants during cardiovascular motion phases.

13. A device for determining the position of a medical instrument introduced into an object to be examined and for imaging the vicinity of the medical instrument, which device includes:

a memory including a stored image data set defining a survey image of the object to be examined including an indication of markers on the patient;

localization means for determining a position of an end zone of a medical instrument, the end zone comprising a portion of the medical instrument that is to be inserted within the object to be examined during use of the medical instrument, a localization device being arrangeable in the end zone of the medical instrument that is to be introduced, imaging means for the acquisition at the same time of image information concerning the vicinity of the medical instrument, an image acquisition device arrangeable on the end zone of the medical instrument, and data processing and display means for displaying the survey image of the object to be examined, the data processing and display means connected to the localization means for determining the position of the localization device, and displaying the position of the medical instrument in the survey image of the object to be examined based on the determined position of the localization device and the markers on the patient indicated in the survey image, and the data processing and display means further comprising means for determining and displaying images of the vicinity of the object to be examined, wherein said images are based on the image information acquired by the image acquisition device.

14. The device as claimed in claim 13, further comprising an electrocardiogram, said data processing and display means comprises means for correcting the determined location of the end zone in response to cardiac motion determined by the electrocardiogram.

* * * * *